United States Patent
Erickson et al.

(10) Patent No.: US 10,252,008 B2
(45) Date of Patent: Apr. 9, 2019

(54) CONTAINER FOR SHARP MEDICAL WASTE

(71) Applicant: ULTIMED INC., Excelsior, MN (US)

(72) Inventors: Thomas E. Erickson, Crosslake, MN (US); James J. Erickson, Mound, MN (US); Thomas P. Sauro, Rosemount, MN (US)

(73) Assignee: ULTIMED INC., Excelsior, MN (US)

( * ) Notice: Subject to any disclaimer, the term of this patent is extended or adjusted under 35 U.S.C. 154(b) by 675 days.

(21) Appl. No.: 14/797,788

(22) Filed: Jul. 13, 2015

(65) Prior Publication Data

US 2015/0313673 A1    Nov. 5, 2015

Related U.S. Application Data

(63) Continuation of application No. 12/392,200, filed on Feb. 25, 2009, now abandoned.
(Continued)

(51) Int. Cl.
*A61M 5/32* (2006.01)
*B65D 85/24* (2006.01)
(Continued)

(52) U.S. Cl.
CPC ....... *A61M 5/3205* (2013.01); *A61B 50/3001* (2016.02); *A61B 50/362* (2016.02);
(Continued)

(58) Field of Classification Search
CPC ... A61B 90/92; A61B 50/362; A61B 50/3001; A61B 2050/0057; A61B 2050/3004;
(Continued)

(56) References Cited

U.S. PATENT DOCUMENTS 3,221,928 A    12/1965    Horn
4,453,648 A    6/1984    Harris et al.
(Continued)

FOREIGN PATENT DOCUMENTS

WO    9631414 A1    10/1996
WO    2005120610 A3    12/2005
(Continued)

OTHER PUBLICATIONS

All non-patent literature documents and foreign patent documents have been previously uploaded in parent U.S. Appl. No. 12/392,200.

*Primary Examiner* — J. Gregory Pickett
*Assistant Examiner* — Brijesh V. Patel
(74) *Attorney, Agent, or Firm* — Seager, Tufte & Wickhem LLP

(57) ABSTRACT

A sharps container for safe storage of used pen needles, pen needle assemblies, syringe needles, syringe needle covers, and combinations thereof having a substantially non-porous housing which includes a receiver which receives and actively conveys external pen needles, pen needle assemblies, syringe needles, syringe needle covers, and combinations thereof into the interior of the housing; an internal storage compartment sized to facilitate the safe storage of a plurality of used pen needles or syringe needles and optional needle covers. The internal storage compartment including a material capable of absorbing and storing fluids which may incidentally be associated with the used pen needles or syringe needles. The receiver for pen needles, pen needle assemblies, syringe needles, syringe needle covers, and combinations thereof is visually distinguished from the surrounding portions of the housing by one or both of having a different color or different color patterning relative to the surrounding housing.

10 Claims, 3 Drawing Sheets

Related U.S. Application Data

(60) Provisional application No. 61/037,973, filed on Mar. 19, 2008.

(51) Int. Cl.

| | | |
|---|---|---|
| *A61B 50/36* | (2016.01) | |
| *A61B 90/92* | (2016.01) | |
| *A61M 5/00* | (2006.01) | |
| *A61B 50/00* | (2016.01) | |
| *A61B 50/30* | (2016.01) | |

(52) U.S. Cl.
CPC .............. *A61B 90/92* (2016.02); *B65D 85/24* (2013.01); *A61B 2050/0057* (2016.02); *A61B 2050/3004* (2016.02); *A61B 2050/3008* (2016.02); *A61B 2050/3013* (2016.02); *A61M 5/002* (2013.01); *A61M 2205/583* (2013.01)

(58) Field of Classification Search
CPC ... A61B 2050/3008; A61B 2050/3013; A61M 5/002; A61M 5/3205; A61M 2205/583; B65D 85/24
USPC .................................. 206/366; 220/502, 529
See application file for complete search history.

(56) References Cited

U.S. PATENT DOCUMENTS

| | | |
|---|---|---|
| 4,580,688 A | 4/1986 | Harris et al. |
| 4,779,728 A | 10/1988 | Hanifl et al. |
| 4,842,138 A | 6/1989 | Sandel et al. |
| 4,874,103 A | 10/1989 | Quisenberry et al. |
| 4,877,150 A | 10/1989 | Otto et al. |
| 4,890,733 A | 1/1990 | Anderson |
| 4,903,832 A | 2/1990 | Stewart |
| 5,046,614 A | 9/1991 | Torres et al. |
| 5,107,990 A | 4/1992 | Wicherski et al. |
| 5,143,210 A | 9/1992 | Warwick et al. |
| 5,152,394 A | 10/1992 | Hughes |
| 5,184,720 A | 2/1993 | Packer et al. |
| 5,190,185 A | 3/1993 | Blechl |
| 5,245,117 A | 9/1993 | Withers et al. |
| 5,330,899 A | 7/1994 | DeVaughn |
| 5,385,105 A | 1/1995 | Withers, Jr. et al. |
| 5,409,113 A | 4/1995 | Richardson et al. |
| 5,469,964 A | 11/1995 | Bailey |
| 5,494,158 A | 2/1996 | Erickson |
| 5,545,145 A | 8/1996 | Clinton et al. |
| 5,603,404 A | 2/1997 | Nazare et al. |
| 5,626,230 A | 5/1997 | Shanley et al. |
| 5,740,909 A | 4/1998 | Nazare et al. |
| 5,971,966 A | 10/1999 | Lay |
| 6,053,314 A | 4/2000 | Pittman |
| RE36,693 E | 5/2000 | Reich |
| 6,685,017 B2 | 2/2004 | Erickson |
| 6,745,898 B2 | 6/2004 | Lin |
| 6,792,662 B2 | 9/2004 | Samuel |
| 6,923,318 B1 | 8/2005 | Erickson et al. |
| 6,923,319 B1 | 8/2005 | Erickson et al. |
| 7,344,027 B2 | 3/2008 | Erickson et al. |
| 7,556,149 B2 | 7/2009 | Erickson et al. |
| 7,694,811 B2 | 4/2010 | Brown et al. |
| 7,694,822 B2 | 4/2010 | Sullivan et al. |
| 7,721,886 B2 | 5/2010 | Erickson et al. |
| 7,789,230 B2 | 9/2010 | Klein |
| 7,815,046 B2 | 10/2010 | Sansoucy et al. |
| 7,891,487 B2 | 2/2011 | Erickson et al. |
| 2006/0243536 A1 | 11/2006 | Tyni et al. |
| 2008/0308411 A1 | 12/2008 | Guo et al. |
| 2009/0236347 A1 | 9/2009 | Erickson et al. |
| 2010/0084293 A1 | 4/2010 | Erickson et al. |
| 2010/0084406 A1 | 4/2010 | Erickson et al. |

FOREIGN PATENT DOCUMENTS

| | | |
|---|---|---|
| WO | 2005120611 A1 | 12/2005 |
| WO | 2008027126 A1 | 6/2008 |

CONTAINER FOR SHARP MEDICAL WASTE

RELATED APPLICATIONS

This application is continuation of U.S. application Ser. No. 12/392,200, filed Feb. 25, 2009, which claims priority to U.S. Provisional Application No. 61/037,973 filed Mar. 19, 2008.

BACKGROUND OF THE INVENTION

A world-wide health care problem and need is the disposal of used syringes; this is a continuing health threat to the public. Of great concern, of course, are AIDS and other serious infectious diseases such as hepatitis. And, needles can become contaminated when used to treat various conditions such as allergies, infertility, arthritis, migraines, HIV, growth hormones among others.

Health care regulations have mandated the safe disposal of used syringes. A number of approaches, procedures and apparatus have been proposed for the storage of used syringes and the subsequent disposal thereof.

After a needle has been used either by or on a patient, then the syringe needle is contaminated from contact with the blood of the patient. If the user is HIV positive or a carrier of hepatitis or other blood born pathogen, then an accidental needle stick by the contaminated needle could spread the disease.

In hospitals and clinics the health care industry uses special containers dedicated for the disposal of needles and other invasive devices. Such containers are frequently referred to as "sharps" containers. The sharps containers with used syringes/needles therein are then disposed by industrial waste collectors and are usually either burned, disintegrated or buried, depending upon local health care regulations.

There is an additional dimension to the problem; that is the uses of syringes in private homes. For example, home syringe users are frequently diabetics who require frequent doses of insulin to regulate their glucose level. The practice of disposing and safe storage of used syringe syringes in private homes is far less organized than in hospitals and clinics. Home disposing techniques are varied and frequently home invented, using discarded or empty containers found around the home; such arrangements are high risk for accidental spreading of disease. There is currently no standard disposal practice for insulin users.

SUMMARY OF THE INVENTION

There is still a need for a sharps container to safely and conveniently contain medical waste such as used syringe needles and pen needles.

Accordingly, the present invention provides a container for sharp medical waste comprising a housing having substantially non-porous walls; an internal storage space sized to facilitate the safe storage of a plurality of used pen needles, pen needle assemblies, and combinations thereof; a material capable of absorbing and storing fluid; means for receiving at least one of pen needles, pen needle assemblies, syringe needles, syringe needle covers, and combinations thereof, wherein the means for receiving pen needles, pen needle assemblies, syringe needles, syringe needle covers, and combinations thereof is visually distinguished from the surrounding portions of the housing; and further wherein the means for receiving at least one of pen needles, pen needle assemblies, syringe needles, syringe needle covers, and combinations thereof may be moved from a first position in communication with the exterior of the container to a second position in communication with the interior of the container to effect a transfer of the at least one of pen needles, pen needle assemblies, syringe needles, syringe needle covers, and combinations thereof from the exterior of the container to the interior of the container. The storage space could also include material to encourage evaporation.

DETAILED DESCRIPTION

The following description should be read with reference to the drawings wherein like reference numerals indicate like elements throughout the several views. The drawings, which are not necessarily to scale, are not intended to limit the scope of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

Medical delivery pens have become widely used in place of, or in addition to, medical syringes, e.g., by diabetics, who frequently inject themselves several times a day with accurately measured, adjustable, pre-selected amounts of insulin or other medication. Medical delivery pens include a reservoir of medication and a distal end adapted to be attached, usually by thread means, to a pen needle assembly. As is well known (see, for example, FIG. 1 of U.S. Pat. No. 5,545,145) the pen needle assembly has, within an outer, generally cylindrical shield, a generally cylindrical housing within which is mounted an axially extending hollow needle, (i) the proximal end of which punctures a seal in the distal end of the medical delivery pen to allow the flow there-through of medication when the delivery pen is screwed into the proximal end of the pen needle cylindrical housing, and (ii) the distal end of which is for insertion into tissue of the person requiring the medication. The pen needle assemblies typically also include (i) a removable thin sterile seal covering the proximal (large diameter) end of the outer shield and (ii) a removable tube-like shield covering the distal portion of the hollow needle. The pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or substitute medication) in liquid form; the correct amount of medication can be determined from prior professional medical instruction or by use of convenient portable blood analysis kits which are small, compact and provide rapid indicators of the user's blood sugar level. Some of the typical several daily injections are often done away from the diabetic's residence which has made the use of the portable, convenient medical delivery pens widespread. The aforesaid testing kits and the medical delivery pens are relatively small in size and can easily fit within a woman's purse or equivalent. A typical scenario for a diabetic at a restaurant for a meal is to first use the blood sugar testing kit to obtain an indicator of his or her blood sugar level. This information then facilitates programming or adjusting the medical delivery pen to deliver the desired quantity of medication. Then the pen with an attached pen needle (a pen needle assembly without the outer cylindrical and tube shields) is used to inject the tissue and dispense the medication. These steps require a relatively short length of time and can be done with minimum loss of privacy.

Some people requiring multiple daily medicine injections use both medical syringes and medical delivery pens with pen needles.

Medical delivery pens are also widely used by doctors, nurses and other professionals in their duties. Many individuals will request that an injection be done with a pen needle rather than a syringe. The aforementioned professionals are especially mindful of possible dangers from a needle stick and the possible unwanted "sticks" that occur in the professional world.

The user, both individual or professional, of a pen needle assembly should, after the first use of a pen needle, carefully detach the used pen needle from the medical delivery pen and safely dispose said pen needle into a safe sharps container. The approved disposal procedure is (i) insertion of the distal end of the needle into the tube-like shield (sometimes omitted) and thence the shielded needle and pen needle cylindrical housing into the outer cylindrical shield, (ii) unscrewing of the medical delivery pen from the proximal end of the pen needle cylindrical housing, and (iii) careful placement of the used pen needle assembly into a safe sharps container. Further, in the "perfect" world, the user of a medical syringe would safely dispose the used syringe into a safe sharps container.

Unfortunately, the recommended safe disposal procedures are not always followed. Used and potentially dangerous syringes, pen needles or pen needle assemblies are routinely left in unsafe places where third parties may unwittingly be "stuck" with possible dire consequences. Examples of such unsafe places are purses, the pockets on the back of aircraft seats, private and public wastebaskets, garbage receptacles, dumpsters and empty milk or other unsafe containers.

Further, the above described pen needle assembly or pen needle disposal procedure requires that the user or associate handle or hold the pen needle while the pen is unscrewed therefrom; this creates the possibility of a potentially dangerous "stick." Also, if the user or associate tries to insert the pen needle into the outer shield to form a pen needle assembly, then additional handling is again required with the possibility of a "stick".

Similar disposal considerations apply to the more traditional syringe needles which may have associated syringe needle covers.

DETAILED DESCRIPTION OF THE INVENTION

Figure 1:
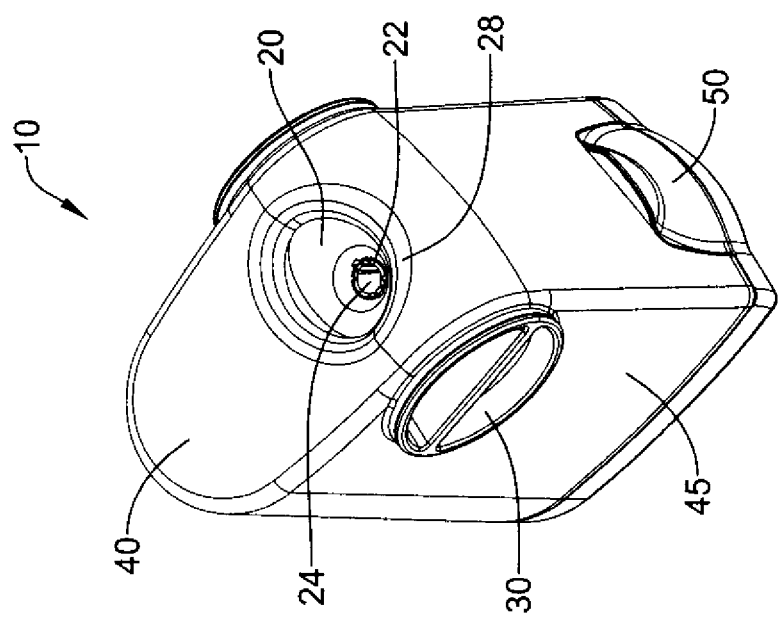
FIG. 1 is a top, side isometric view of a sharps container provided by the invention.

In FIG. 1, a multi-functional sharps container 10 provides a single apparatus for the safe storage and disposal of used pen needles and for the storage of unused pen needles. The container is adapted for single handed operation which allows a used pen needle to be removed and stored without touching the pen needle. This minimizes the risk of "sticks". It will be appreciated that a similar apparatus, not illustrated, may provide similar functions for used syringe needles. The details of the embodiment of FIG. 1 are provided for the purpose of illustrating features of the invention and should not be considered limiting. The sharps container 10 has a top 40, sides 45, and a bottom. Generally, the components of the container are locked, e.g., by adhesive and/or latches, to prevent opening the container or otherwise providing access to used pen needles. The container 10 includes a funnel-shaped or frustoconical receiving means 20 which assists the user in aligning and inserting the used pen needle and attached medical delivery pen into a receiving aperture 24 and an optional ejector mechanism 22. The container may also include a generally mating frustoconical segment 28 which provides a larger entry target. In some embodiments, the receiving aperture 24 and/or ejector mechanism 28 includes features, such as protrusions and recesses, which engage corresponding features of the pen needle to prevent rotation thereof as the medical delivery pen is rotated to disengage the pen needle. This allows the insertion or the pen needle into the receiving means and the subsequent removal of the used pen needle from the medical delivery pen to be readily performed with a single hand while the container rests on a suitable surface. Following removal of the pen needle from the medical delivery pen and removal of the medical delivery pen, the handle 30 may be rotated, clockwise or counterclockwise, to invert the attached receiving means 20 and receiving aperture 24 which allows the pen needle to fall or be ejected from the receiving aperture 24, with or without the assistance of optional ejector mechanism 28. Under some circumstances, the user may have covered the used pen needle with a cover to re-form a pen needle assembly and may have manually removed the pen needle assembly. In that case, it is useful for the combination of receiving means 20 and receiving aperture 24 to have a combined depth and configuration to accommodate both the used pen needle and the associated cover of the pen needle assembly in at least one orientation and convey them to the internal storage compartment when the handle 30 is rotated.

Figure 2:
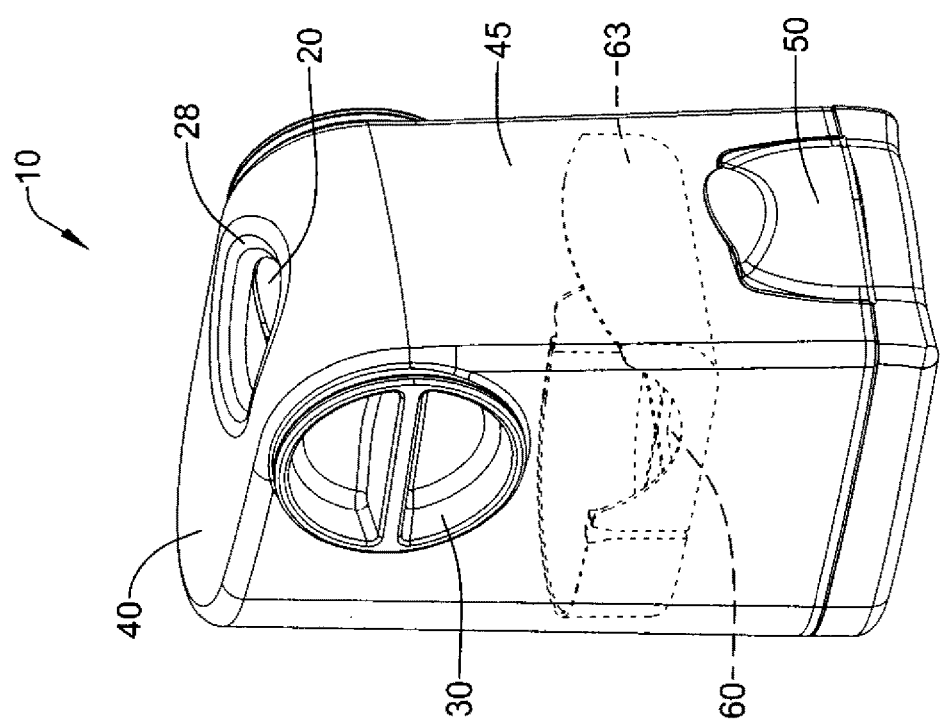
FIG. 2 is side, top isometric view of the same sharps container.

In addition to the features already discussed, FIG. 2 illustrates an interior partition 60, shown in phantom, which divides the container into separate compartments for storing used pen needles and unused pen needle assemblies. In the container illustrated, the lower compartment is for unused pen needle assemblies and door 50 opens to provide access to the storage compartment for unused pen needle assemblies. The partition may be fixed in a single position or may move to alter the ratio of storage volume in the two compartments as unused needle assemblies are removed, used, and returned to the container with or without the associated pen needle cover. Partition 60 may also include a fluid absorbing layer 63 to minimize leakage of any fluids which may remain in or on the used pen needles.

Figure 3:
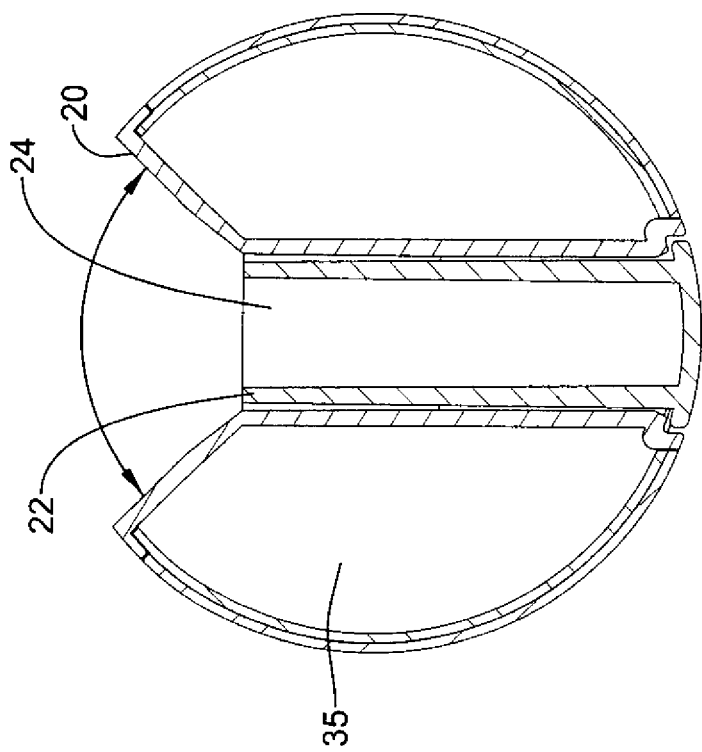
FIG. 3 is a cross-sectional view of a rotatable component of the container.

FIG. 3 is an illustrative transverse cross-section of receiving means 20, ejector mechanism 28, and receiving aperture 24 as they are located in barrel 35 between handles 30. In this embodiment, rotation of the handle 30 conveys the used pen needle within the used pen needle storage portion of the container 10 where the ejector mechanism 28 displaces it from the receiving aperture 24. A variety of suitable ejector means are known to those of skill in the art and may be selected to function with other design details.

In one embodiment, a material capable of absorbing and storing fluid associated with the container is selected from organic or inorganic absorbing materials. Any of the known of fluid absorbing materials and forms may be used providing they have sufficient capacity to hold liquids which may incidentally be introduced into the container along with the pen needles and/or syringe needles to be stored. The following group of materials is intended to be illustrative and non-limiting. Powders of desiccants such as silica gel, calcium sulfate, calcium chloride, montmorillonite clay, and molecular sieves or organic materials such as polyacrylic acid, polymethacrylic acid, polyacrylamide, and polyalkylene oxide may be provided alone or in layered constructions with a liquid permeable sheet. The polymers may conveniently be provided as nonwoven pads or as powders. In addition to homopolymers such as those listed, the fluid absorbing material may be copolymers and/or optionally may be crosslinked. The absorbent material may be associated with one or more of the floor and/or walls of the internal storage space. In certain embodiments, the fluid absorbent material within the container has a fluid capacity of at least 0.75 ml for each pen needle or syringe needle to be stored. In other embodiments, the fluid absorbent material within the container has a fluid capacity of at least 0.25 ml for each pen needle or syringe needle to be stored. In yet other embodiments, the available fluid capacity per pen needle or syringe needle may be reduced based upon assumptions regarding the rate of evaporation of fluids from the container and the rate at which additional pen needles or syringe needless are added to the container so long as sufficient capacity is present to absorb the fluid associated with each new pen needle or syringe needle deposited.

In some embodiments, the means for receiving pen needles, pen needle assemblies, syringe needles, syringe needle covers, and combinations thereof is generally frustoconical as seen from the exterior of the container. In this context, "frustoconical" should be broadly interpreted to include frusta of cones having bases other than circles. The bases may be, for example, ellipses, regular or irregular polygons or other closed curves. In some embodiments, the lateral surface of the cone may be described as formed by straight line segments moving along the base, however in other embodiments, the surface may be formed by moderately curved lines. The cone may be a right cone or may be an oblique cone. Generally it is believed that the walls of the cone should form approximately a 45 degree angle with the axis of an inserted pen needle or syringe to provide both a broad entry aperture and a good degree of guidance for the insertion of the pen needle or syringe needle into the device. In some embodiments, the frustoconical receiving portion of the disposal container may smoothly join a similar frustoconical portion of the housing when the receiving portion is positioned to receive a pen needle, pen needle assembly, syringe needle, syringe needle cover, or combinations thereof in at least one position of the frustoconical portion relative to the housing.

Particularly in those embodiments in which a pen needle assembly or syringe needle cover is to be inserted axially into the frustoconical receiving portion of the container, it is generally desirable that the frustoconical portion have a height sufficient to contain a pen needle assembly or syringe needle cover within the frustoconical portion. This height will often be greater than the height necessary to contain only a pen needle or syringe needle and may be seen as allowing the receiving portion to rotate to a position within the container without undue interference with the housing.

In some embodiments, the portion of the container which receives pen needles, pen needle assemblies, syringe needles, syringe needle covers, and combinations thereof provides a visual contrast to the surrounding portions of the housing to aid visually impaired users in properly orienting and inserting the pen needles, pen needle assemblies, syringe needles, syringe needle covers, and combinations thereof. The visual distinctive feature may be provided in the form of color contrast and/or patterning relative to the surrounding housing. Preferably, the color associated with the receiving region or a patterned portion thereof will be red.

In some embodiments, the means for receiving pen needles includes a combination of protrusions and recesses which engage the pen needle to prevent rotation thereof as a pen is rotated relative to the pen needle within the said means. This engagement facilitates one hand removal of a pen needle from a medical delivery pen, thereby minimizing the risk of accidental sticks.

In some embodiments, the means for receiving pen needles, pen needle assemblies, syringe needles, syringe needle covers, and combinations thereof includes a means for rotating the receiving means relative to the housing. In certain embodiments, the rotation will be about an axis generally perpendicular to an axis associated with the pen needle, pen needle assembly, syringe needle, syringe needle cover, or combinations thereof which are to be conveyed into the interior storage space. In other embodiments, the rotation will be about an axis which is generally parallel to an axis associated with the pen needle, pen needle assembly, syringe needle, syringe needle cover, or combinations thereof which are to be conveyed into the interior storage space. The means for rotating the receiving means may be either manual or automated as by a spring drive or electric motor.

In some embodiments, the means for receiving pen needles, pen needle assemblies, syringe needles, syringe needle covers, and combinations thereof includes an ejector assembly having an ejector axis and wherein the means for receiving pen needles, pen needle assemblies, syringe needles, syringe needle covers, and combinations thereof is operatively coupled to the means for rotating said receiving means relative to the housing. In those embodiments, it is preferred that rotation of the receiving means convey the pen needles, pen needle assemblies, syringe needles, syringe needle covers, and combinations thereof within the internal storage space whereupon the ejector assembly ejects the pen needle, pen needle assembly, syringe needle, syringe needle cover, or combinations thereof from the receiving means into the internal storage space.

In some embodiments, the container includes one or more guards which prevent pen needles, pen needle assemblies, syringe needles, syringe needle covers, or combinations thereof within the internal storage space from re-entering the means for receiving and ejecting pen needles, pen needle assemblies, syringe needles, syringe needle covers, and combinations thereof. This is desirable to prevent accidental or intentional removal of sharps from the internal storage space, particularly when the container is inverted or otherwise placed in an orientation other than that normally employed for disposing of sharps. Absent such guards, sharps might accidentally released during transport. In certain embodiments, the one or more guards are structures within the internal storage space which prevent access to the receiving means in positions other than those associated with receiving or ejecting pen needles, pen needle assemblies, and combinations thereof.

In yet other embodiments, the container includes storage for unused pen needles or needles. In some of those embodiments, the storage for unused pen needles or needles may be accessed by a door having a first position and a second position, wherein the structure of the door renders it stable in either the first position or a second position. A suitable door may be formed by providing an anchoring segment and a door segment joined along a line. The line may function as a living hinge and may be a thinned section between the door segment and the anchoring segment. In the first position, the door and the anchoring segment form a generally continuous panel which is convex outward. In one embodiment, the join line is generally perpendicular to a line which bisects the door and is slightly arched with respect to that line. The stiffness of the material from which the door and the anchoring segment are formed as well as the curvature tend to maintain the door in a first position in which the door and anchoring segment form a single curved surface. As the door is opened, the join line buckles and the door and anchoring segment assume a second position in which the door is planar or even somewhat convex in the immediate vicinity of the join line which tends to hold the door in a stable open position. In certain embodiments, container includes dispensing means for unused pen needles or syringe needles.

In some embodiments, the container includes a partition separating the internal storage space from a storage space for unused pen needles, pen needle assemblies, syringe needles, syringe needle covers, and combinations thereof which is moveable from a first position to a second position. In further embodiments, the volumetric ratio between the internal storage space and the unused pen needle or syringe needle storage space may be adjusted as the ratio of the volume of used pen needles, pen needle assemblies, syringe needles, syringe needle covers, and combinations thereof to the volume of unused pen needles or syringe needles changes. The change in volumetric ratio may be continuous or discrete. It may occur automatically or may be adjusted manually. In other embodiments, the container includes a means for indicating the fraction of the available internal storage space that is currently occupied by used unused pen needles, pen needle assemblies, syringe needles, syringe needle covers, and combinations thereof. The indicating means may be provided in any convenient way. For example, a translucent case would allow the level of visually contrasting used sharps within the internal storage space to be seen to a sufficient degree. Other options may include counters and moving strip indicators.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A container for sharp medical waste comprising:
   a housing having non-porous walls defining a container volume;
   an interior partition including a material capable of absorbing and storing fluid, moveable within the container volume, which interior partition divides the container volume into:
   a first internal storage volume sized to facilitate the safe storage of a plurality of used pen needles, pen needle assemblies, and combinations thereof; and
   a second internal storage volume sized to facilitate the safe storage of a plurality of unused pen needles, pen needle assemblies, and combinations thereof,
   wherein movement of the interior partition within the container volume serves to vary a ratio of the volume of the first internal storage volume to the volume of the second internal storage volume;
   a receiver having a barrel sized and adapted to accommodate the insertion therein of the entirety at least one of a pen needle, a pen needle assembly, a syringe needle, a syringe needle cover, and combinations thereof,
   wherein the receiver is located within the housing and in communication with the first internal storage volume,
   wherein a portion of the receiver adapted to accommodate the insertion therein of the entirety at least one of a pen needle, a pen needle assembly, a syringe needle, a syringe needle cover, and combinations thereof is frustoconical in presentation to the exterior of the housing and includes a visual distinction from surrounding portions of the housing,
   wherein the visual distinction from the surrounding portions of the housing is that at least one of the color of the portion of the receiver is different from the color of the surrounding portions of the housing or the color pattern of the portion of the receiver is different from the color pattern of the surrounding portions of the housing,
   further wherein the barrel of the receiver is adapted to be moved by rotation of a handle from a first position in communication with the exterior of the container to a second position in communication with the first internal storage volume to effect a transfer of the at least one of pen needles, pen needle assemblies, syringe needles, syringe needle covers, and combinations thereof from the exterior of the container to the first internal storage volume, whereupon the at least one of pen needles, pen needle assemblies, syringe needles, syringe needle covers, and combinations thereof is ejected from the barrel of the receiver when the receiver is moved to the second position.

2. The container of claim 1, wherein the material capable of absorbing and storing fluid is selected from inorganic desiccants or hydrophilic organic materials.

3. The container of claim 2, wherein the material within the container is capable of absorbing and storing fluid has a fluid capacity of at least 0.75 ml for each pen needle and syringe needle to be stored therein.

4. The container of claim 2, wherein the material within the container is capable of absorbing and storing fluid has a fluid capacity of at least 0.25 ml for each pen needle and syringe needle to be stored therein.

5. The container of claim 1, wherein the frustoconical portion of the receiver has a height sufficient to contain a pen needle assembly within the frustoconical portion.

6. The container of claim 1, wherein the frustoconical portion of the receiver is colored, at least in part, red.

7. The container of claim 1, wherein the housing has a frustoconical portion which provides an extension of the receiver portion frustoconical in presentation to the exterior of the container in at least one position of the frustoconical portion of the receiver.

8. The container of claim 1 wherein the second internal storage volume is accessible by a door having a first position and a second position, wherein the door position is stable in either the first position and a second position.

9. The container of claim 1, wherein the interior partition separating the first internal storage volume from the second internal storage volume moves from a first position to a second position as the ratio of a volume of used pen needles, pen needle assemblies, syringe needles, syringe needle covers, and combinations thereof within the housing to a volume of unused pen needles, pen needle assemblies, syringe needles, syringe needle covers, and combinations thereof within the housing changes.

10. The container of claim 1, comprising an indicator for indicating a fraction of the first internal storage volume which is occupied.

* * * * *